US006743966B2

(12) United States Patent
Smith

(10) Patent No.: US 6,743,966 B2
(45) Date of Patent: *Jun. 1, 2004

(54) PRODUCTION OF MEMBRANE PROTEINS IN THE MILK OF TRANSGENIC MAMMALS

(75) Inventor: Alan E. Smith, Boston, MA (US)

(73) Assignee: Genzyme Corporation, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/185,269

(22) Filed: Jun. 27, 2002

(65) Prior Publication Data

US 2003/0033618 A1 Feb. 13, 2003

Related U.S. Application Data

(63) Continuation of application No. 09/627,290, filed on Jul. 28, 2000, now Pat. No. 6,472,584, which is a continuation of application No. 08/088,416, filed on Jul. 7, 1993, now Pat. No. 6,448,469, which is a continuation of application No. 07/770,204, filed on Oct. 2, 1991, now abandoned.

(51) Int. Cl.$^7$ .............................................. A01K 67/027

(52) U.S. Cl. ............................ 800/14; 800/15; 800/16; 800/18

(58) Field of Search .............................. 800/7, 14, 15, 800/16, 1; 435/69.1, 320.1, 328; 436/22, 23; 554/8

(56) References Cited

U.S. PATENT DOCUMENTS

| | | | |
|---|---|---|---|
| 4,873,316 A | 10/1989 | Meade et al. | 530/412 |
| 5,240,846 A | 8/1993 | Collins et al. | 435/240.1 |
| 5,304,489 A | 4/1994 | Rosen | 435/320.1 |
| 5,322,775 A | 6/1994 | Clark et al. | 435/69.1 |
| 5,574,206 A | 11/1996 | Jolicoeur | 800/2 |
| 5,589,604 A | 12/1996 | Drohan et al. | 800/2 |
| 6,448,469 B1 * | 9/2002 | Smith | 800/7 |
| 6,472,584 B1 * | 10/2002 | Smith | 800/7 |

FOREIGN PATENT DOCUMENTS

| | | |
|---|---|---|
| EP | 0 264 166 | 4/1988 |
| EP | 0 446 017 | 9/1991 |

OTHER PUBLICATIONS

Anderson, M. et al., (1991) "Generation of cAMP–Activated Chloride Currents by Expression of CFTR" *Science*, 251:679–682.
Andres, A.C. et al., (1987) "Ha–ras Oncogene Expression Directed By a Milk Protein Gene Promoter: Tissue Specificity, Hormonal Regulation, and Tumor Induction in Transgenic Mice" *Proc. Natl. Acad. Science*, USA, 84:1299–1303.

Bagley, R.G. et al., (1994) "Delivery of Purified, Functional CFTR to Epithelial Cells In Vitro Using Influenza Hemagglutinin" in Late–Breaking Science Platform Presentations and Posters, Eighth Annual North American Cystic Fibrosis Conference (abstract).
Buhler, Th. et al., (1990) "Rabbit β–Casein Promoter Directs Secretion of Human Interleukin–2 Into the Milk of Transgenic Rabbits" *Bio/Technology*, 8:140–143.
Clark et al., *Bio/Technology*, vol. 7 (May 1989) pp. 487–492.
Clark, A.J. et al., (1987) "Pharmaceuticals from transgenic livestock" *Tibtech*, 5:20–24.
Clark, A.J. et al., (1989) "Expression of Human Anti–Hemophilic Factor IX in the Milk of Transgenic Sheep" *Bio/Technology*, 7:487–492.
Cosman et al., *Mol Immunol.* vol. 23, No. 9 (1986) pp. 935–941.
Denman, J. et al. (1991) "Transgenic Expression of a Variant of Human Tissue–Type Plasminogen Activator in Goat Milk: Purification and Characterization of the Recombinant Enzyme" *Bio/Technology*, 9:839–843.
DiTullio, P. et al. (1992) "Production of Cystic Fibrosis Transmembrane Conductance Regulator in the Milk of Transgenic Mice" *Bio/Technology*, 10:74–77.
Ebert, K.M. et al., (1991) "Transgenic Expression of a Variant of Human Tissue–Type Plasminogen Activator in Goat Milk: Generation of Transgenic Goats and Analysis of Expression" *Bio/Technology*, 9:835–838.
Gordon, K. et al., (1987) "Production of Human Tissue Plasminogen Activator in Transgenic Mouse Milk" *Bio/Technology*, 5:1183–1187.
Gregory, R. et al., (1990) "Expression and characterization of the cystic fibrosis transmembrane conductance regulator" *Nature*, 347(6291):382–386.
Harris et al., "Gene expression in the mammary gland", *J. Reprod. Fert.* (1990) 88:707–715.
Hennighausen, L.G. (1982) "Characterization and Cloning of the mRNAs Specific for the Lactating Mouse Mammary Gland" *Eur. J. Biochem*, 125:131–141.
Houdebine, Louis–Marie, "Production of Pharmaceutical Proteins from Transgenic Animals" *Journal of Biotechnology*, vol. 34, pp. 269–287.
Imam, A. et al., (1981) "Isolation and Characterization of a Major Glycoprotein From Milk–Fat–Globule Membrane of Human Breast Milk" *Biochem. J.*, 193:47–54.
Jolicoeur et al., "Efficient production of human immunodeficiency virus proteins in transgenic mice" *Journal of Virology*, vol. 66, No. 6, pp. 3904–3908.
Kartner, N. et al., (1991) "Expression of the Cystic Fibrosis Gene in Non–Epithelial Invertebrate Cells Produces a Regulated Anion Conductance" *Cell*, 64–681–691.

(List continued on next page.)

*Primary Examiner*—Deborah Crouch
(74) *Attorney, Agent, or Firm*—Fish & Richardson, P.C.

(57) ABSTRACT

Production of proteins not normally secreted through conventional pathways such as membrane proteins including, for example, CFTR associated with cystic fibrosis, is now made possible by collection of such protein from the milk of lactating transgenic animals.

19 Claims, 8 Drawing Sheets

OTHER PUBLICATIONS

Kerem, B. S. et al., (1989) "Identification of the Cystic Fibrosis Gene: Genetic Analysis" *Science*, 245:1073–1080.

Krimpenfort et al., "Generation of Transgenic Dairy Cattle Using In Vitro Embryo Production" *Biotechnology*, vol. 9, pp. 844–847.

Meade, H. et al., (1990) "Bovine $Alpha_S$–Casein Gene Sequences Direct High Level of Expression of Active Human Urokinase in Mouse Milk" *Bio/Technology*, 8:443–446.

Mullins et al., "Transgenesis in Nonmurine Species" *Hypertension*, vol. 22, No. 4, pp. 630–633.

Patton, S. et al., (1986) "A Method for Isolation of Milk Fat Globules" *Lipids*, 21(2):170–174.

Patton S. et al., (1975) "The Milk Fat Globule Membrane" *Biochem. Biophys. Acta*, 415:273–309.

Rich et al., *Nature*, vol. 347 (Sep. 27, 1990) pp. 358–363.

Riordan, J. et al., (1989) "Identification of the Cystic Fibrosis Gene: Cloning, and Characterization of Complementary DNA" *Science*, 245:1066–1073.

Rommens, J.M. et al., (1989) "Identification of the Cystic Fibrosis Gene: Chromosome Walking and Jumping" *Science*, 245:1059–1065.

Sasaki, M. et al., (1978) "Lactose and Major Milk Proteins are Present in Secretory Vesicle–Rich Fractions From Lactating mammary Gland" *Proc. Natl. Acad. Sci. USA*, 75(10):5020–5024.

Suda et al., "Induction of a variety of tumors by c–erbB2 and clonal nature of lymphomas even with the mutated gene (Va1659__Glu569)", *The EMBO Journal*, vol. 9, No. 1, pp 181–109.

Van Brunt, J. (1988) "*Molecular Farming: Transgenic Animals as Bioreactors*" *Bio/Technology*, 6:1149–1154.

Wall, R.J., "Transgenic Livestock: Progress and Prospects for the Future" *Theriogenology*, vol. 45, pp. 57–68.

* cited by examiner

PRODUCTION OF MEMBRANE PROTEINS IN THE MILK OF TRANSGENIC MAMMALS

This application is a continuation of U.S. application Ser. No. 09/627,290, filed Jul. 28, 2000 now is U.S. Pat. No. 6,472,584; which is a continuation of U.S. application Ser. No. 08/088,416, filed Jul. 7, 1993 now U.S. Pat. No. 6,448,469; which is a continuation of U.S. Pat. No. 07/770,204, filed Oct. 2, 1991 abandoned, the contents of which are incorporated herein by reference.

FIELD OF INVENTION

The present inventions involves the large-scale production of membrane specific proteins and more particularly involves the production of such proteins using transgenic animals and most specifically involves the production of CFTR, the protein involved with Cystic Fibrosis.

BACKGROUND OF THE INVENTION

Striking progress has been made in our understanding of cystic fibrosis (CF) during the period since the gene associated with the disease was identified[1-3]. Many mutations within the gene have been identified in DNA from patients with CF[4-10]. The protein product of the gene, named CFTR, has been identified[11] and functional studies have shown that CFTR cDNA is able to complement the defect in ion transport characteristic of cells from CF patients[12,13]. The domain structure of CFTR has been probed by analysis of mutated versions of the protein [14-18]. Such studies indicate that CFTR is a Cl⁻ channel [14,19,20] and that it is regulated by phosphorylation of the R-domain[16,18,21] and by nucleotide binding[22]. To our knowledge none of such proteins have involved exogenous or recombinant membrane proteins.

SUMMARY OF THE INVENTIONS

In accordance with the principles of the present invention it has been surprisingly discovered that exogenous or recombinant membrane proteins can be produced in the milk of transgenic animals. In the most preferred embodiment of the present invention, recombinant CFTR has been produced in the milk of transgenic mice containing CFTR cDNA downstream of a mammary specific promoter. Most preferred embodiments will employ larger transgenic animals including, for example, rabbits, goats, sheep and cows which produce large quantities of milk however, the development of such animals takes considerably longer than the time periods required for developing transgenic mice. While the time periods vary considerably, the procedures and methods are substantially identical.

Other embodiments include the apocrine like secretion in tissue culture of membrane proteins by cells which have been maintained in a differentiated state. Such proteins would be secreted as part of the membrane released during the "pinching off" proces. Membrane proteins suitable for production according to the methods of the present include receptors, channels, viral glycoproteins, transporters and other proteins typically associated with cellular membranes. Such membrane proteins can be used for therapeutics such as by administration of the abnormally deficient or missing protein, or by use as vaccines in the case of viral glycoproteins including for example utilization of the envelope of HIV, Herpes Virus or influenza in order to develop immunity with respect to infection caused thereby.

Advantageously, methods of the present invention can also be employed for the production of membrane proteins useful for diagnostic purposes. For example, one could use the present methods to produce the receptor for thyroid stimulating hormone (TSHR) which would be useful for the diagnosis of Graves Disease. Such proteins could also be used to screen for therapeutically active compounds.

Preferred methods of the present invention will employ promoters, ideally coupled with suitable enhancers, that are mammary specific so that production of the desired membrane protein is incorporated into milk fat globules which will appear in the milk of a lactating female transgenic animal. Such an animal is, of course, by definition, reproductively competent. Greater appreciation of these and other emodiments will be acquired by study of the following drawings, examples and detailed procedures.

BRIEF DESCRIPTION OF THE FIGURES

Further understanding of the present invention may be had by reference to the figures wherein.

DETAILED DESCRIPTION AND BEST MODE

Figure 1A:
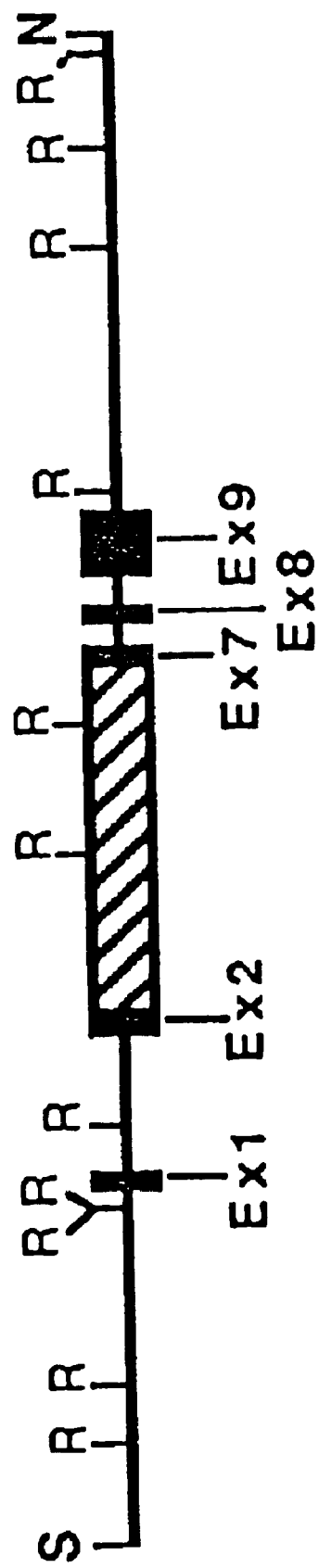
FIG. 1(a) shows the structure of the mammary specific expression vector for producing CFTR using abbreviations: S, Sal I; R, EcoR I; N, Not I.

The 17.8 Kb DNA construct used to produce transgenic mice capable of secreting CFTR in their milk is shown in FIG. 1A. It consists of a full length copy of CFTR cDNA (containing a point mutation at residue 936 to inactivate an internal cryptic bacterial promoter that otherwise renders the cDNA unstable[15] ) inserted between exons 2 and 7 of the goat β-casein gene. The β-casein gene contains a mammary gland specific promoter which results in expression of the desired gene, e.g. CFTR or other membrane protein, within the mammary gland. Other milk specific promoters which may be used in substitution include well known promoters such as α-casein, whey acid protein and β-lactoglobulin promoters. Most preferred constructs will include one or more enhancer elements typically associated with such genes as has been described previously in the art. Such promoters/enhancers are then associated with the coding sequence of the membrane protein of interest using conventional recombinant techniques. Such coding sequence may be either cDNA, partial or fully genomic DNA but more preferably either of the latter two categories since such have been shown in transgenic systems to cause greater levels of expression. More particularly, the 4.5 kb Sal I-Sal I fragment from pMT-CFTR[15] was cloned into the Xho I site of CAS 1441 (see also FIG. 5C). The cosmid vector CAS 1441 contains an altered goat β-casein gene with an Xho I site in place of the coding portion of the gene. Earlier studies have characterized the goat casein gene and shown that it directs the synthesis of a number of gene products in the milk of both transgenic mice and goats in a tissue-specific manner[26,]

27. The portion deleted extends from the Taq I site in exon 2 to the PpuM I site in exon 7.

Figure 5A:
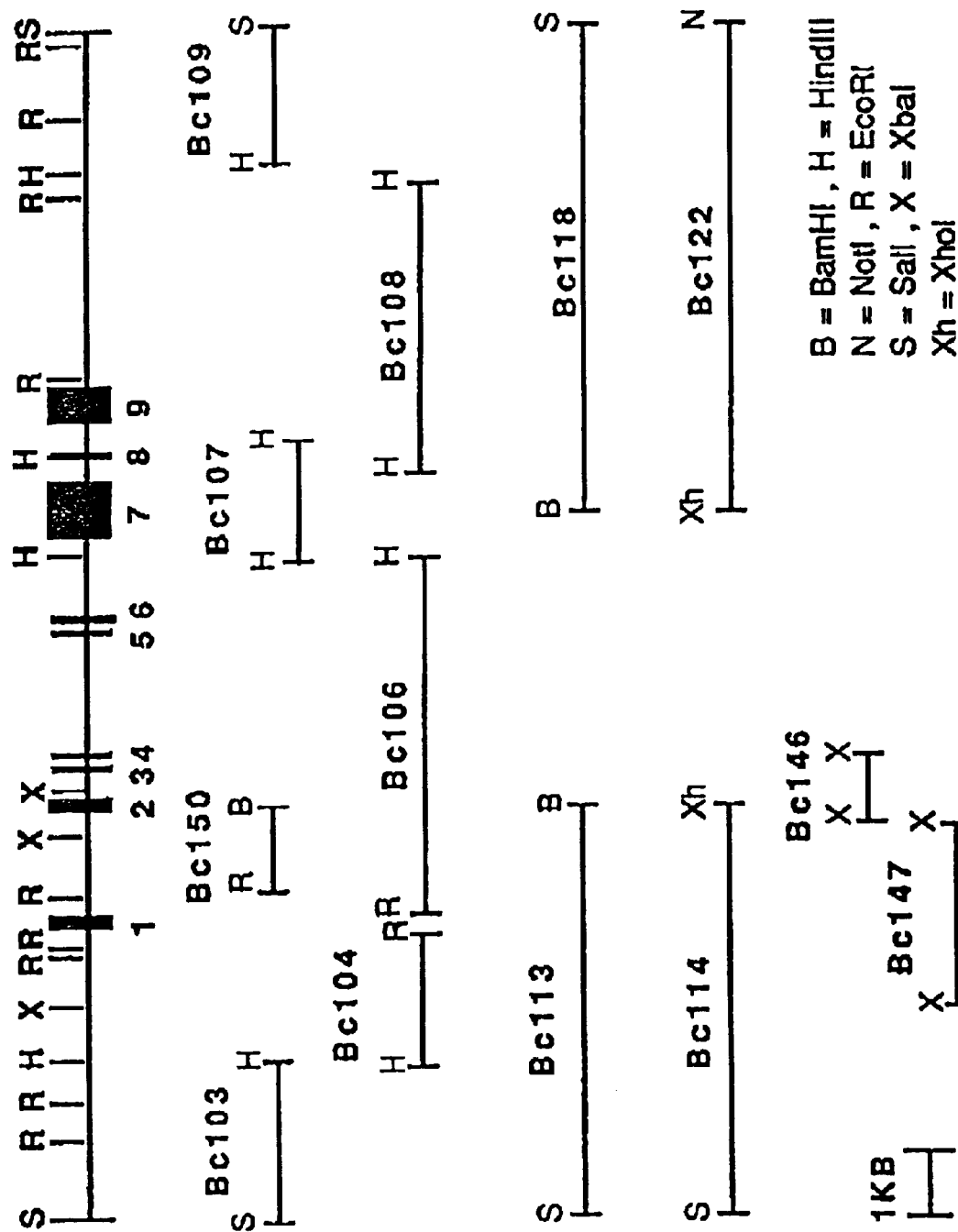
FIGS. 5A, B and C graphically show relevant vector constructions.

With further reference to Figure series 5, a goat genomic DNA library was constructed by cloning DNA fragments generated by partial MboI digestion of Saanen goat DNA into EMBL3 phage as described by Maniatis et al. 31. The library, consisting of 1.2×106 recombinant phage, was screened with a 1.5 Kb HindIII/TthIII1 DNA fragment encoding the entire mouse beta casein cDNA as described by Maniatis et al. 31. Three plaques designated 3–7, 3–8, and 3–11 exhibited the strongest hybridization signals under conditions of high stringency and each were subjected to three rounds of plaque purification. Restriction enzyme and Southern blotting analysis revealed that the inserts within recombinant phage 3–7 and 3–8 were subfragments of the 18.5 Kb insert contained in phage 3–11. Therefore, all DNA fragments used for construction of a mammary gland specific expression vector were derived from clone 3–11 which is shown in FIG. 5A. All subclones were constructed in pUC or pUC derivatives with modified polylinker.

To construct a mammary gland specific expression vector, the entire upstream (5' portion) region from the SalI site to exon 2 and the entire downstream (3' portion) region from exon 7 to the SalI site of the goat beta casein gene was used to direct expression to the mammary gland. To engineer the 5' end of the beta casein gene, the TaqI site in exon 2 of clone Bc106 was replaced with a BamHI restriction site to produce the plasmid Bc150 (FIG. 5A). The entire available 5' region of the goat beta casein gene was constructed by the sequential addition of the subclones Bc104, Bc147, and Bc103 (FIG. 5A). The orientation of subclone Bc147 was verified by restriction analysis. The final vector designated Bc113 contains a SalI site at the 5' end and a BamHI site at the 3' end. The downstream BamHI was subsequently changed to an XhoI site to form Bc114.

The 3' end of the goat beta-casein gene was constructed in a similar fashion to the 5' end. The 1.8 Kb Bc108 clone (FIG. 5A) was digested with PpuMI to allow for the addition of a BamHI linker. The BamHI/HindIII fragment from the engineered clone Bc108 was ligated into the vector Bc109 which contained the extreme 3' flanking region of the goat beta casein gene. The entire 3' end was completed by the addition of the 4.4 Kb HindIII fragment from Bc108 was cloned into the modified Bc109 vector and screened for orientation. The new vector was designated Bc118 and contained the entire 3' region of beta casein from exon 7 through the poly A signal and 5 Kb downstream to the SalI site of EMBL clone 3–11. Subsequently, an XhoI site was introduced at the 5'BamHI site and a NotI site at the 3' SalI site of Bc118 to produce the vector Bc122.

Figure 5B:
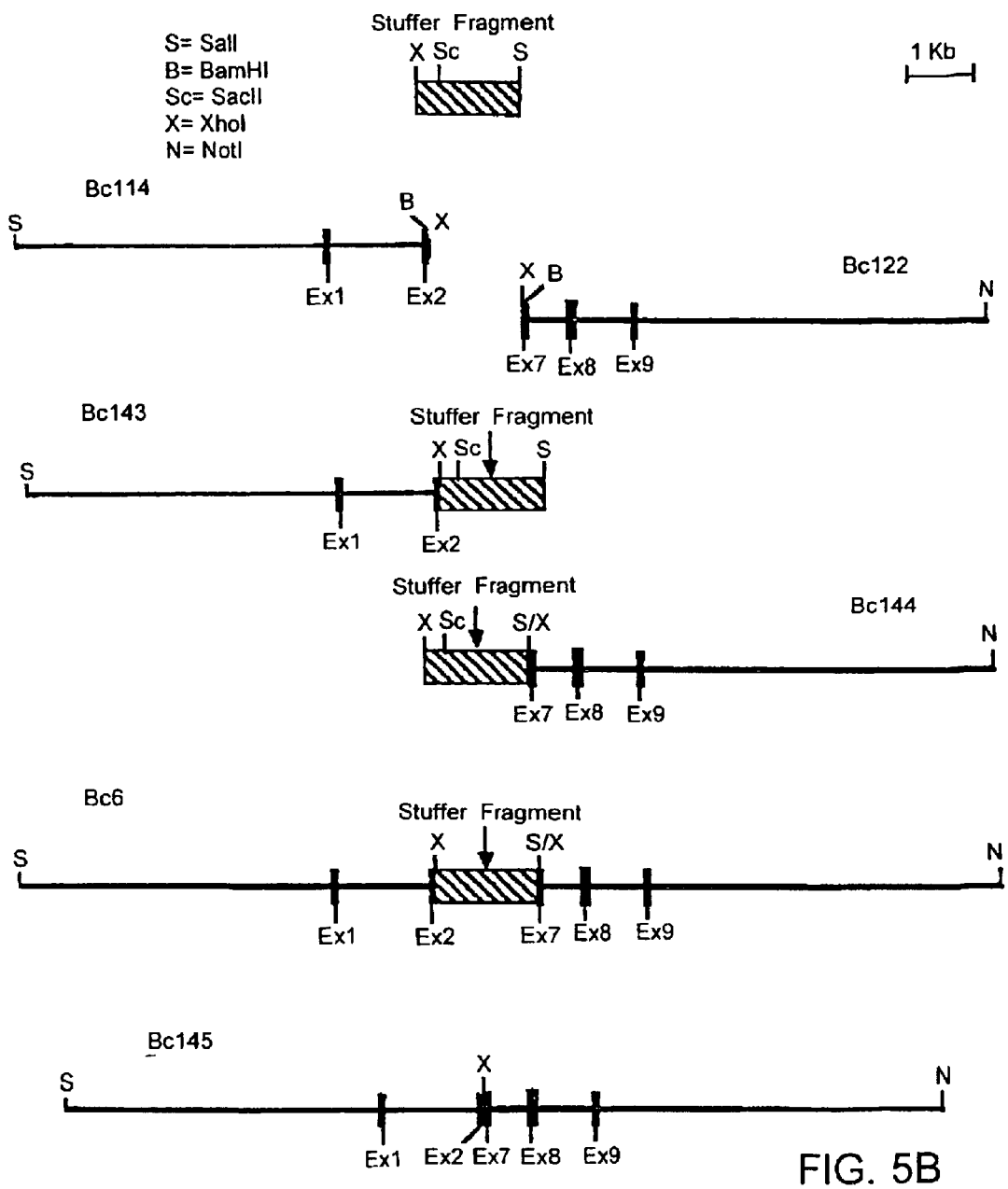
Figure 5C:
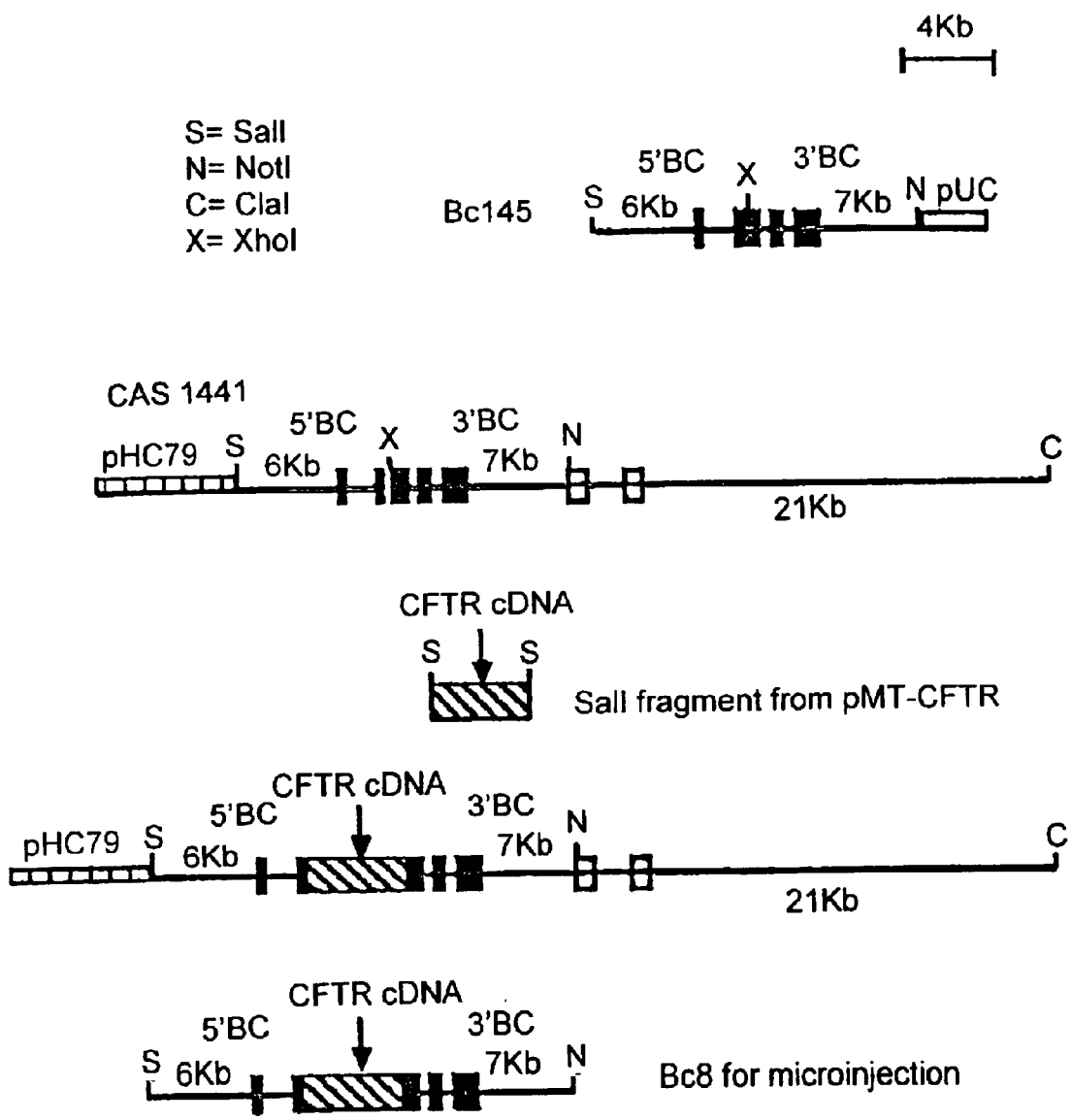

The overall cloning strategy followed to construct the beta casein CFTR vector (Bc8) is shown in FIG. 5B and 5C. To construct a goat beta casein vector containing all the available upstream and downstream sequences, a 1.7 Kb XhoI to SalI stuffer fragment containing a unique SacII site cloned into the XhoI site of Bc114 and Bc122 to form vectors Bc143 and Bc144, respectively. The complete vector was made by cloning the SalI to SacII fragment from Bc143 into a SalI to SacII cut Bc144 to form the plasmid Bc6. The stuffer fragment was removed from the plasmid by digestion with BamHI and a unique XhoI site was inserted to form the vector Bc145. The SalI to NotI fragment from Bc145 which contains the 5' and 3' beta casein sequences was subcloned into the cosmid clone CAS1438 to form the cosmid CAS1441. CAS1438 is a cosmid vector constructed in pHC79 containing an engineered SalI and NotI site and 21 Kb of 5' flanking sequence from the Bovine alpha-casein gene[32] (Meade et al. Biotechnology 8, 443–45 1990). The expression vector Bc8 was constructed by digesting the vector CAS1441 with XhoI and ligating in the 4.5 Kb SalI fragment from pMT-CFTR[11,17]. Orientation of the CFTR cDNA was confirmed by restriction analysis. To obtain a fragment for microinjection, the vector Bc8 was digested with SalI and NotI to release the beta casein CFTR portion of the vector for purification. The final microinjection fragment contained 4.2 Kb of 5' flanking sequence, exon 1, intron 1, a portion of exon 2, 4.5 Kb CFTR cDNA, a portion of exon 7, intron 7, exon 8, intron 8, exon 9, and 5.3 Kb of 3' flanking sequence. This fragment from Bc8 was injected into mouse embryos and reimplanted using standard methods. Transgenic mice were identified by Southern blot analysis of DNA from the tails of resulting offspring.

To screen for positive transgenic mice, approximately 15 μg of genomic DNA from each founder mouse was digested with EcoR I, separated on a 1% agarose gel, transferred to magnagraph nylon (Fisher Scientific and hybridized with the 384 bp Pvu II-Pvu II fragment from exon 7 of the mouse β-casein cDNA[30] and the 4.5 kB SalI I-SAI fragment of pMT-CFTR. Copy number was quantitated using a Betascope 603 Analyzer.

Figure 1B:
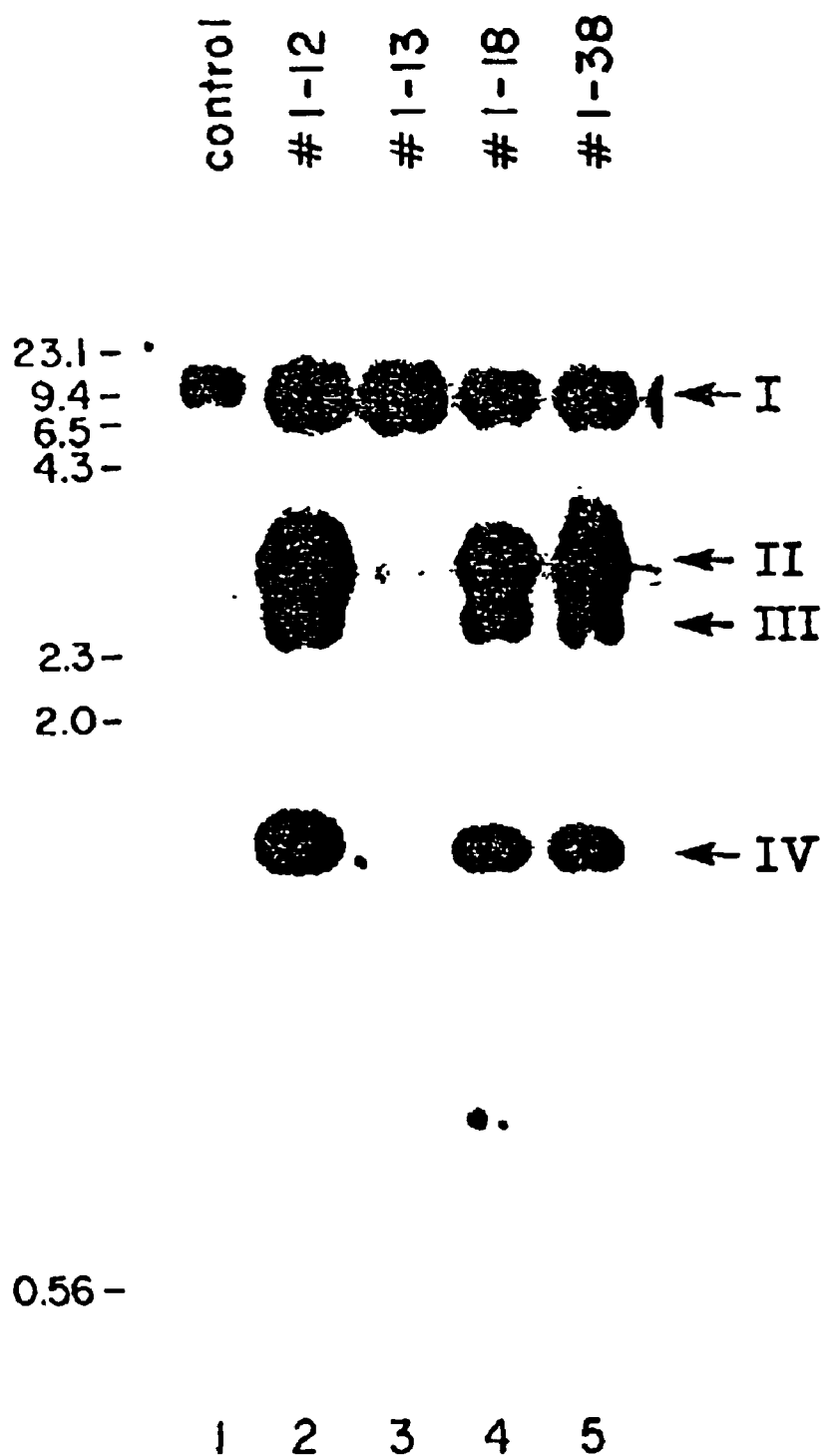
FIG. 1(b) shows identification of positive transgenic mice by Southern blot analysis.

FIG. 1B shows DNA from the positive founder animals. Band I is mouse β-casein DNA and bands II, III and IV are CFTR DNA. Lane 1 is a control mouse and lanes 2 to 5 show results of four founder transgenic mice. Such analysis indicates the copy number of the transgene in the lines varied between 1 and 10.

Founder mice were bred to produce lactating transgenic females. Milk from such animals was collected, diluted with PBS (phosphate buffered saline) and treated with RIPA (50 mM Tris-HCI [pH 7.5], 150 mM NaCI, 1% Triton X-100, 1% sodium deoxycholate and 0.1% sodium dodecyl suplhate) buffer to solubilize membrane proteins. Briefly, samples were examined for the presence of CFTR by immunoprecipitation with pAbEx13, a highly purified polyclonal antibody raised against an R-domain fusion protein (see Canadian Patent Application 2,037,478-1, fully incorporated herein by reference), followed by in vitro phosporylation treatment of the washed immunoprecipitate with protein kinase A(PKA) in the presence of $[_\gamma{}^{32}P]ATP$[11,15]. More specifically, procedures for preparing cell lysates immunoprecipitation of proteins using pAbEx13, one-dimensional peptide analysis and SDS-polyacrylamide gel electrophoresis were as described by Cheng et al. [15,16]. In vitro phosphorylation of the CFTR-containing immunoprecipitates was achieved by incubating with protein kinase A and $[_\gamma{}^{32}P]ATP$ (10 μCi) in a final volume of 50 μl in kinase buffer (50 mM Tris-HCI, pH 7.5, 10 mM $MgCl_2$ and 100 μg $ml^{-1}$ bovine serum albumin) at 30° C. for 60 min. Milk was collected from the transgenic mice at days 3, 5, 7 and 9 of lactation. Mice were injected with oxytocin (2.5 IU) and milked 5 min later with a suction device. The milk was diluted (10 fold) and solubilized in RIPA buffer prior to immunoprecipitation.

Figures 2A, 2B:
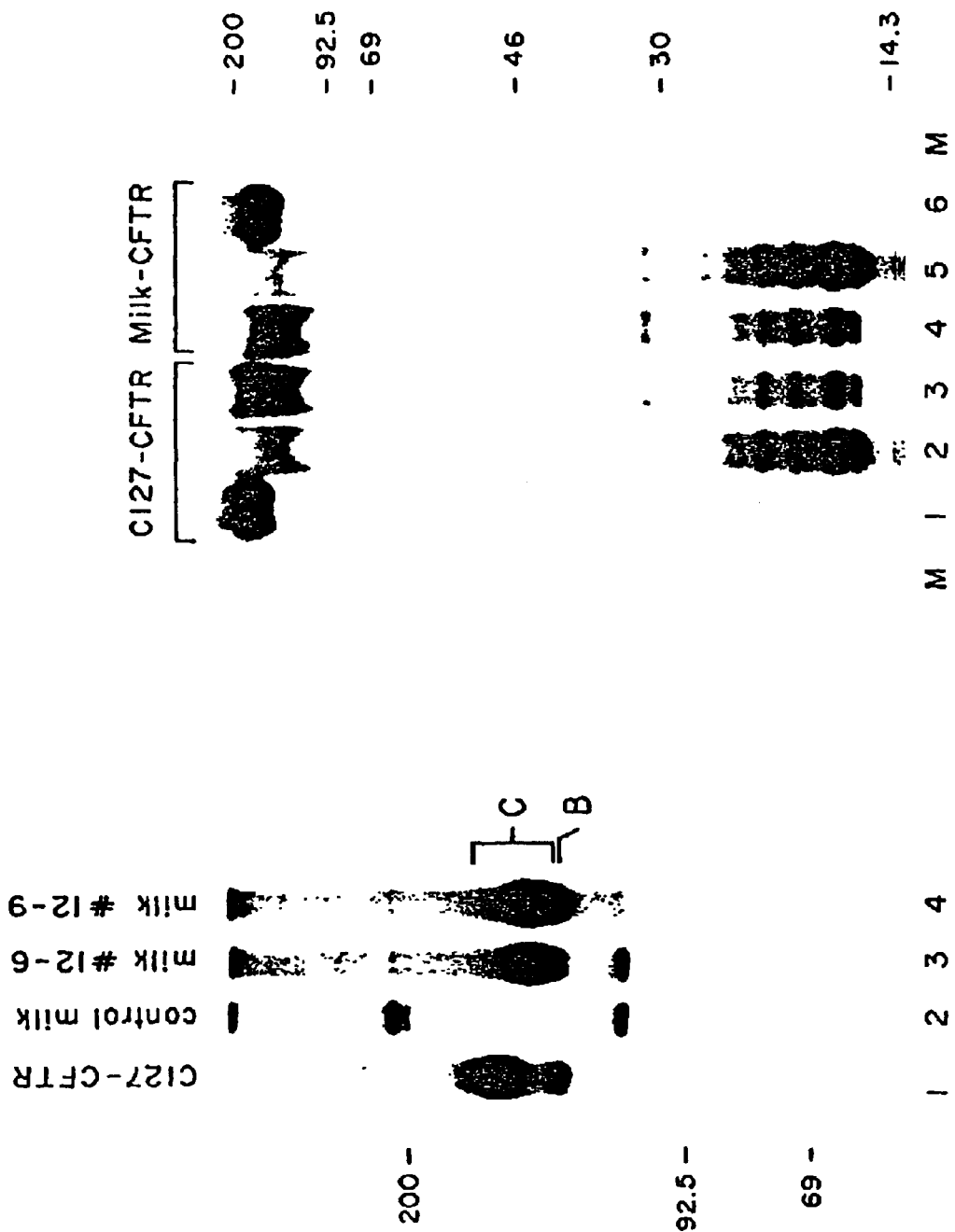
FIG. 2(a) shows the detection of CFTR in milk of transgenic mice.
FIG. 2(b) shows one-dimensional peptide analysis of CFTR synthesized in recombinant C127 cells and in transgenic mice milk.

FIG. 2A shows a polyacrylamide gel of samples from milk of two females of line #12 and a control mouse. Lane 1 contains an iminunoprecipitate from approximately 3×10⁶ recombinant C127 cells stably transfected with a wild type CFTR cDNA. Immunoprecipitates of 50 μl of control milk (lane 2), milk from transgenic mouse #12-6 (lane 3) and mouse #12-9 (lane 4) were subjected to the same treatment. The positions of the fully processed CFTR (band C) and the partially glycosylated form (band B) are indicated on the right margin. Exposure time was 30 min at –70° C. As can be seen from the results, a diffuse band of labeled protein is detected in the milk from both of the transgenic mice but not the control. The protein (lanes 3 and 4) migrates slightly more rapidly than the fully processed version of CFTR (lane 1) from stably transfected mouse C127 cells containing a BPV-CFTR vector. Such differences in migration of CFTR have been detected previously in samples of the protein from various recombinant and high producer cells. They have been shown to be caused by differences in glycosylation[15, 20].

To confirm that the protein detected in FIG. 2(*a*) is indeed CFTR, the labeled protein was eluted and subjected to partial proteolytic cleavage using *Staphylococcus aureus* V8 protease followed by polyacrylamide gel analysis. Specifically, the vitro labeled bands C from recombinant C127 cells (lanes 1–3) and from mouse #12-6 (lanes 4–6) were excised from the gel and digested with different amounts of *Staphylococcus aureus* V8 protease[11,15]. Proteins in lanes 2 and 5 were digested with 0.17 $\mu g\ \mu g^{-1}$ *S. aureus* V8 protease and those in lanes 3 and 4 with 0.017 $\mu g\ \mu l^{-1}$ enzyme. Lanes 1 and 6 were untreated samples. Exposure time was 24 h at −70° C. The results depicted in FIG. 2(*b*) show that the milk derived protein yields a fingerprint indistinguishable from that of CFTR derived from C127 cells. Thus, the milk from line #12 mice contained authentic CFTR. Similar analysis of milk from the other transgenic mouse lines for the presence of CFTR showed that line #38 contained CFTR but in lesser amounts than in line #12 whereas lines #18 and #13 contained no detectable protein.

To confirm that the difference in mobility between milk-derived and C127 cell-derived CFTR results from different patterns of glycosylation, the $^{32}$P-labeled proteins were subjected to digestion with N-Glycanase® enzyme, endoglycosidase H and endoglycosidase F. In particular, the CFTR immunoprecipitated from the milk of transgenic mouse #12-9 and from recombinant C127 cells were phosphorylated in vitro using protein kinase A and [$_\gamma^{32}$P]ATP. Following elution from polyacrylamide gels, the CFTR proteins were either subjected to no treatment (lanes 1, 3, 5 and 7) or were incubated with N-Glycanase (lanes 2 and 4), endoglycosidase H (lane 6) or endoglycosidase F (lane 8). Samples were separated by electrophoresis and analyzed by autoradiography. The positions of the fully processed form of CFTR (band C) and the non-glycosylated version (band A) are indicated on the right margin. Exposure was for 24 h at −70° C. The enzymes N-Glycanase, endoglycosidase H and endoglycosidase F were from Genzyme Corp. Conditions for digestion with the respective glycosidases were as specified by the manufacturer, except that incubations were performed at 37° C. for 4 h only. CFTR was immunopurified using the polyclonal antibody pAb Ex13, phosphorylated in vitro with protein kinase A and [$_\gamma^{32}$P]ATP, separated on SDS-polyacrylamide gels, and then extracted from the gels by macerating the gel pieces in protein extraction buffer (50 mm ammonium bicarbonate, 0.1% sds and 0.2% β-mercaptoethanol). Eluted proteins were recovered by trichloroacetic acid precipitation.

Figure 3:
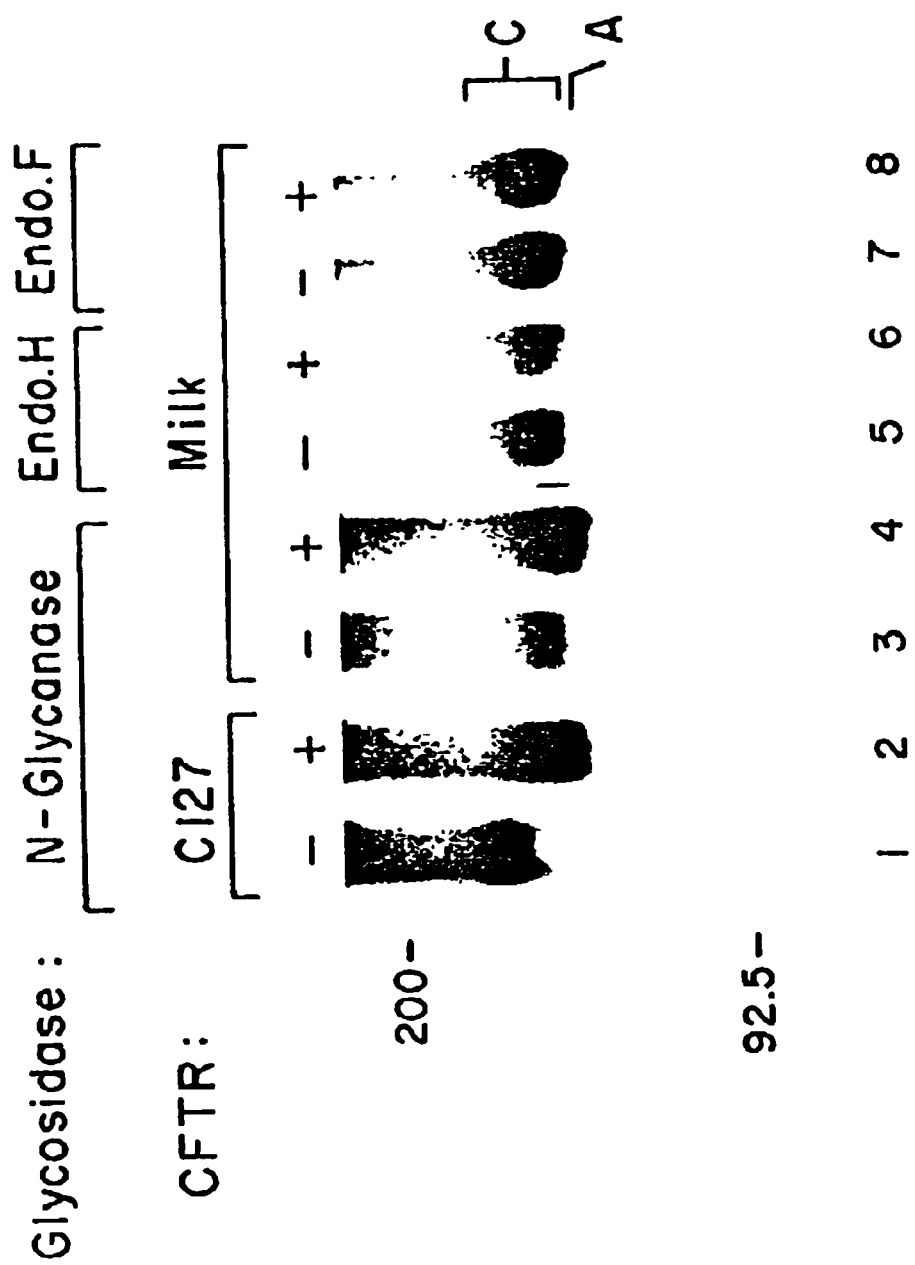
FIG. 3 shows the digestion of milk-derived CFTR with glycosidases.

The results depicted in FIG. 3 show that milk CFTR is digested by N-glycanase to yield a band of greater mobility (lane 2) that co-electrophoreses with the corresponding band from C127 cell-derived, N-glycanase-treated CFTR (lanes 4). This band consisted of non-glycosylated CFTR[11,15]. As shown previously for COS-7 derived CFTR[15], milk derived protein is resistant to cleavage by endoglycosidase H or F (lanes 6 and 8). It is therefore clear that the protein detected in the milk of transgenic mice is a fully glycosylated form of CFTR that contains carbohydrate side chains of somewhat less complexity than CFTR from recombinant C127 cells. In separate studies tissue plasminogen activator (tPA) produced in recombinant cells has been compared with that produced in milk of transgenic goats and likewise shown to have differences in the pattern of glycosylation[26].

We surprisingly discovered that membrane proteins such as CFTR can be expressed in milk. We discovered that CFTR is present in the membrane of milk fat globules and thus is found in the lipid-rich fraction of the milk, that is, in the cream. To isolate the CFTR, milk from transgenic animals was fractionated as described by Imam et al. and Patton & Huston[29]. In summary, milk was first centrifuged at 3000 g to separate the cream which floats from the skim milk. The bulk of the caseins were separated from the skim milk by further low speed centrifugation at 12,000 g. Since milk fat globules are fragile, some membrane fragments remain in the supernatant of centrifuged skim milk[23,29]. Such residual membrane vesicles and fragments were collected by further high speed centrifugation at 100,000 g. In detail, 0.4 volume of wash buffer (10 mM Tris-HCI, pH 7.5, 0.25 M sucrose and 1 MM MgCl$_2$) was added to whole milk (approximately 300 $\mu$l) and centrifuged at 3000 g for 15 min at room temperature to separate the cream. The resulting skim milk was siphoned off by inserting a needle through the layer of cream. The cream was washed twice with approximately 5 volumes of wash buffer and dispersed in RIPA buffer. The siphoned skim milk was centrifuged at 12,000 g for 10 min to pellet the caseins. The casein pellet was washed once with 5 volumes of wash buffer and resuspended in RIPA buffer. Membranes and vesicles contained in the resultant skim supernatant were collected by further centrifugation at 100,000 g for 2 h.

Figure 4:
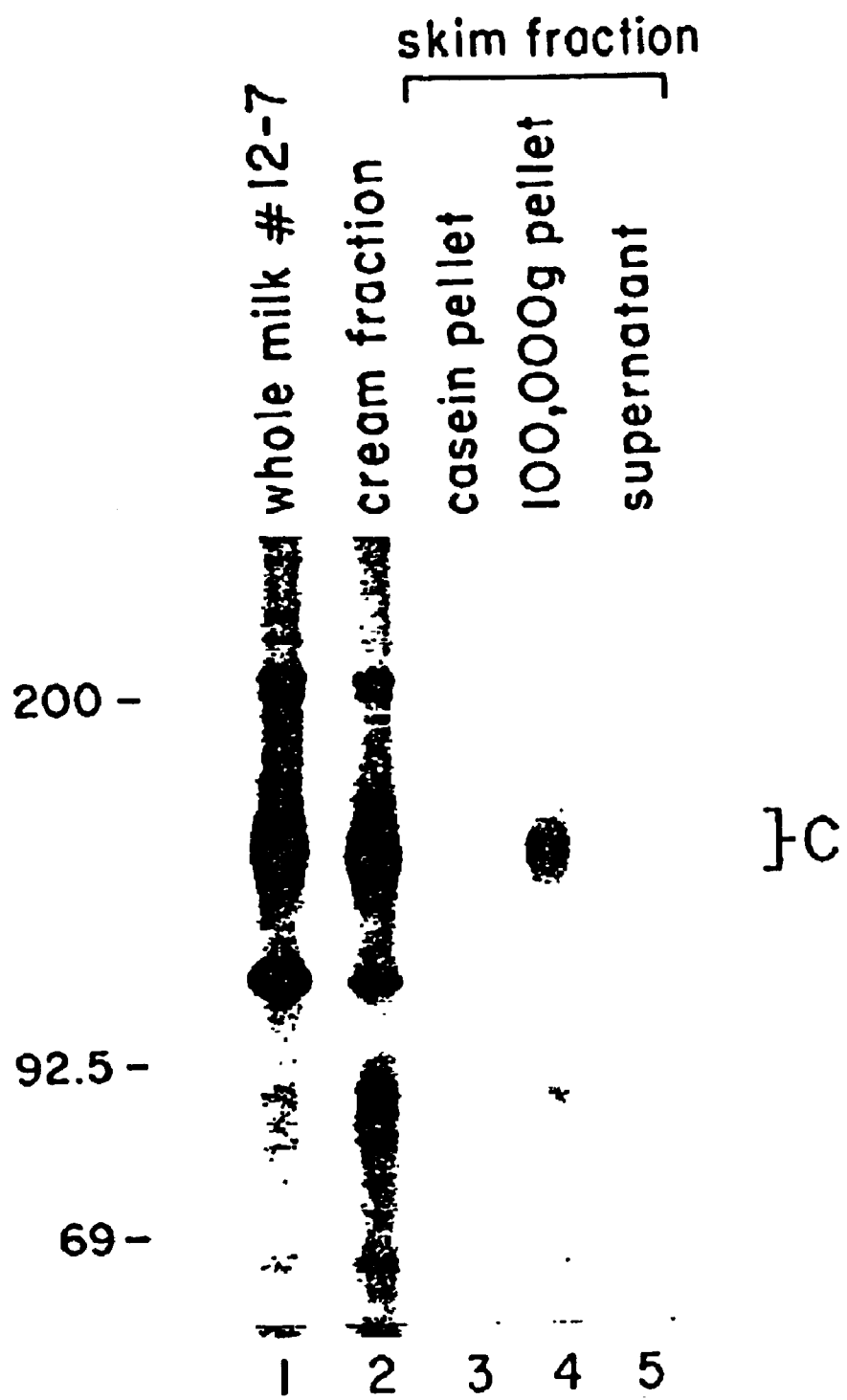
FIG. 4 shows fractionation of milk from transgenic mice.

FIG. 4 shows PKA immunoprecipitation assays of the various fractions obtained. Whole milk (lane 1), the cream fraction (lane 2), the casein-containing pellet (lane 3), the 100,000 g skim pellet (lane 4) and the 100,000 g skim supernatant (lane 5) were solubilized with RIPA buffer, immunoprecipitated with pAb EX13 and phosphorylated in vitro using protein kinase A and ($_\gamma^{32}$P)ATP. Exposure time was 1 h at −70° C. About 65% of the CFTR was present in the cream (lane 2) and the remaining CFTR was in the high speed pellet from the skim milk fraction (lane 4). Virtually no CFTR was present in the casein fraction nor in the high speed supernatant.

The data shown hear clearly indicates that authentic CFTR can be produced in the milk of transgenic mice. The form of protein produced represents mature fully glycosylated CFTR rather than a partially glycosylated intracellular intermediate as indicated by its insensitivity to endoglycosidase H but sensitivity to N-glycanase. This pattern of sensitivity implies CFTR has a carbohydrate structure consistent with it having traversed both the endoplasmic reticulum and the Golgi, but why is it present in the milk ?

This surprising and unexpected result must occur because some, perhaps all, mature CFTR must reach the apical plasma membrane of mammary epithelia in lactating animals. This epithelia is actively involved in high level secretion, not only of soluble milk proteins such as the caseins through the normal protein secretion pathway, but also of lipids in the form of fat globules[23,24]. It has been discovered therefore that CFTR is secreted by apocrine like secretion into the milk rather than remaining in the cellular membrane. If the CFTR is not secreted as a soluble protein, but as part of the milk fat globule. Such globules are composed of an outer covering of pinched-off plasma membrane, a small amount of underlying cytoplasm comprising the so-called cytoplasmic crescent and a globule of fat[23,24]. Whether CFTR is incorporated into the fat globule membrane by a random process of plasma membrane blebbing or whether it is actively recruited to the exiting vesicle as it pinches off remains unknown. The demonstration that most CFTR in milk floats away from the bulk of milk proteins upon centrifugation, and the remainder separates from casein and can be sedimented at high speed strongly suggests that CFTR is present in membrane structures some of which include fat globules. The most plausible explanation of the results is that the bulk of CFTR exits the cell in the membrane of milk fat globules and that some of these globules break off membrane vesicle fragments upon handling. Alternatively, perhaps some empty membrane vesicles containing CFTR but no fat globules are directly shed from the mammary epithelia.

As a result of the present discovery that CFTR can be sequestered into milk, it will be readily apparent to those skilled that other human membrane-associated proteins such as receptors (e.g. cytokine receptors, hormone receptors), viral glycoproteins, transporters and channels that sort at least in part to the apical surface may be produced by the transgenic methods of the present invention. Alternatively, such membrane related proteins can be produced in vitro such as by tissue culture of appropriate cells capable of apocrine secretion. Mammary cells maintained in a differentiated state would be the preferred embodiment of such an approach. Although any cell capable of blistering or "blebbing-off" membrane associated proteins such as those associated with apocrine secretion will suffice. Previous demonstration that the synthesis of soluble human proteins in transgenic milk can be scaled up to production in transgenic goats[26,27] confirms that virtually unlimited amounts of membrane proteins could be produced by this means.

The application of the present invention to CFTR production will enable the development of new therapies for CF. Of direct implication is the capability to now produce sufficient CFTR protein to allow therapeutic treatment of CF patients by protein replacement. In such therapy, CFTR protein is administered to the airway cells, preferably by aerosolization and inhalation, typically in conjunction with helper agents to assist in delivery the CFTR to the airway cell surfaces through the mucous layer for incorporation into the airway cell membrane. Because there is turnover of such cells, treatment by this modality is a continuous prospect.

Other exciting opportunities now enabled by the present invention include protein replacement therapies for other defective or deficient membrane protein mediated diseases as well as diagnostic and screening assays previously made impossible due to the absence of commercially viable membrane protein production systems since membrane proteins are not secreted into the surrounding medium. For example, the ability to now produce identified and sequenced cytokine receptors allows one to create not only an assay with a substrate (using either purified receptor or the milk fat globule itself or membranes therefrom having the receptor exposed) specific for the cytokine (whose binding to the substrate could be readily detected by a labeled, cytokine specific antibody) but can also be used as a screening device to detect other proteins or peptides capable of binding to the same receptors. Such peptides might serve to activate the receptor or alternately as antagonists to prevent cytokine function. Selection of new effective drugs would be facilitated using such a screening approach. Similarly, these techniques would be equally useful for hormone receptors such as those specific for thyroid stimulating hormone as earlier mentioned.

REFERENCES

1. Kerem, B. -S. et al., Science 245, 1073–1080 (1989).
2. Riodan, J. et al., Science 245 1059–1065 (1989).
3. Rommens, J. M. et al., Science 245, 1059–1065 (1989).
4. Cutting, G. R. et al., Nature 346, 366–369 (1990).
5. Dean, M. et al.,, Cell 61, 863–870 (1990).
6. Kerem, B. -S. et al., Proc. Natl. Acad. Sci. USA 87, 8447–8451 (1990).
7. Kobayashi, K., Knowles, M. R., Boucher, R. C., O'Brien, W. E. & Beaudet, A. L. (1990). Am. J. Hum Genet. 47, 611–615 (1990).
8. White, M. B. et al., Nature 322, 467–470 (1990).
9. Devoto, M. et al., Am. J. Hum. Genet. 48, 1127–1132 (1991).
10. Zielenski, J. et al, Genomics 10, 229–235 (1991).
11. Gregory, R. J. et al., Nature 347, 382–386 (1990).
12. Rich, D. P. et al., Nature 347, 358–363 (1990).
13. Drum, M. L. et al., Cell 62, 1227–1233 (1990).
14. Anderson, M. P. et al., Science 253, 202–205 (1991).
15. Cheng, S. H. et al., Cell 63, 827–834 (1990).
16. Cheng, S. H. et al., Cell 66, 1027–1036 (1991).
17. Gregory, R. J. et al., Mol. Cell. Biol. 11, 3886–38983 (1991).
18. Rich, D. P. et al., Science 235, 205–207 (1991).
19. Anderson, M. P., Rich, D. P., Gregory, R. J., Smith, A. E. & Welsh, M. J. Science 251 679–682 (1991).
20. Kartner, N. et al., Cell 64, 681–692 (1991).
21. Tabcharani, J. A., Chang, X. B., Riordan, J. R. & Hanrahan, J. W. Nature 352, 628–631 (1991).
22. Anderson M. P. et al., Cell (in press)
23. Patton, S. & Keenan, T. W. Biochim. Biophys. Acta 415, 273–309 (1975).
24. Keenan, T. W., Franke, W. W., Mather, J. H. & Morre, D. J. In: Lactation. (B. A. Larson, ed.) Academic Press, Inc., New York, 4, 405–436 (1978).
25. Sasaki, M., Eigel, W. N. & Keenan, T. W. Proc. Natl. Acad. Sci. USA 75, 5020–5024 (1978).
26. Denman, J. et al., Bio/Technology 9, 839–843 (1991).
27. Ebert, K. M. et al., Bio/Technoloogy 9, 835–838 (1991).
28. Imam, A., Laurence, D. J. R. & Neville, A. M. Biochem. J. 193, 47–54 (1981).
29. Patton, S. & Huston, G. E. Lipids 21, 170–174 (1986).
30. Yoshimura, M., Banerjee, M. R. & Oka, T. Nuci. Acids Res. 14, 8224 (1986).
31. Maniatis, T., E. F. Fritsch, and J Sambrook. Molecular cloning. A Laboratory Manual. Cold Spring Harbor Laboratory, Cold Spring Harbor, N.Y., 1982.
32. Meade et al. Biotechnology 8,443–45 1990.

What is claimed is:

1. A transgenic non-human mammal which contains within its genome a DNA sequence comprising, as operably linked components, a DNA sequence encoding a membrane protein and a mammary gland specific promoter sequence, wherein, upon expression of the DNA sequence, the membrane protein inserts into an apical membrane of a mammary epithelial cell of the mammal, thereby producing the membrane protein in the milk of the mammal.

2. The mammal of claim 1, wherein the mammary gland specific promoter is a beta-casein promoter.

3. The mammal of claim 1, wherein the mammary gland specific promoter is a beta lactoglobulin promoter.

4. The mammal of claim 1, wherein the mammary gland specific promoter is an alpha-casein promoter.

5. The mammal of claim 1, wherein the mammary gland specific promoter is a whey acid protein promoter.

6. The mammal of claim 1, wherein the membrane protein is a transmembrane ion channel protein.

7. The mammal of claim 1, wherein the membrane protein is selected from the group consisting of a transmembrane ion channel, a hormone receptor protein, a thyroid stimulating hormone receptor, a cytokine receptor protein, and a viral glycoprotein.

8. The mammal of claim 1, wherein the mammal is selected from the group consisting of a mouse, a rabbit, a goat, a sheep and a cow.

9. A transgenic non-human mammal which contains within its genome a DNA construct comprising, as operably linked components, a DNA sequence encoding a membrane protein and a beta casein promoter sequence, wherein, upon expression of said DNA sequence, the membrane protein inserts into an apical membrane of a mammary epithelial cell of the mammal, thereby producing the membrane protein in the milk of the mammal.

10. The mammal of claim 9, wherein the membrane protein is a transmembrane ion channel protein.

11. The mammal of claim 9, wherein the membrane protein is selected from the group consisting of a transmembrane ion channel, a hormone receptor protein, a thyroid stimulating hormone receptor, a cytokine receptor protein, and a viral glycoprotein.

12. The mammal of claim 9, wherein the mammal is selected from the group consisting of a mouse, a rabbit, a goat, a sheep and a cow.

13. A transgenic non-human mammal which contains within its genome a DNA sequence comprising, as operably linked components, a DNA sequence encoding said a cystic fibrosis transmembrane conductance regulator protein and a mammary gland specific promoter sequence, wherein, upon expression of the DNA sequence, the cystic fibrosis transmembrane conductance regulator protein inserts into an apical membrane of mammary epithelial cell of the mammal, thereby producing the cystic fibrosis transmembrane conductance regulator protein in the milk of the mammal.

14. The mammal of claim 13, wherein the mammary specific promoter is a beta-casein promoter.

15. The mammal of claim 13, wherein the mammary gland specific promoter is a beta-lactoglobulin promoter.

16. The mammal of claim 13, wherein the mammary gland specific promoter is an alpha-casein promoter.

17. The mammal of claim 13, wherein said mammary gland specific promoter is a whey acid protein promoter.

18. The mammal of claim 13, wherein the cystic fibrosis transmembrane conductance regulator protein is mature and fully glycosylated.

19. The mammal of claim 13, wherein the mammal is selected from the group consisting of a mouse, a rabbit, a goat, a sheep and a cow.

* * * * *